United States Patent
Lee

(10) Patent No.: US 10,207,931 B2
(45) Date of Patent: Feb. 19, 2019

(54) FUNCTIONALIZED REDUCED GRAPHENE OXIDE AND METHODS OF PRODUCING THE SAME

(71) Applicant: RESEARCH & BUSINESS FOUNDATION SUNGKYUNKWAN UNIVERSITY, Suwon-si (KR)

(72) Inventor: Hyoyoung Lee, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/926,261

(22) Filed: Mar. 20, 2018

(65) Prior Publication Data

US 2018/0208468 A1  Jul. 26, 2018

Related U.S. Application Data

(60) Division of application No. 15/263,948, filed on Sep. 13, 2016, now Pat. No. 10,046,972, which is a continuation-in-part of application No. 14/567,177, filed on Dec. 11, 2014, now abandoned.

(30) Foreign Application Priority Data

Jun. 11, 2014 (KR) .................. 10-2014-0070860

(51) Int. Cl.
| | | |
|---|---|---|
| *C07D 303/00* | (2006.01) | |
| *C01B 32/198* | (2017.01) | |
| *C07F 5/02* | (2006.01) | |
| *C07D 493/22* | (2006.01) | |
| *C01B 32/194* | (2017.01) | |
| *C01B 32/192* | (2017.01) | |
| *C01B 32/23* | (2017.01) | |

(52) U.S. Cl.
CPC .......... *C01B 32/198* (2017.08); *C01B 32/192* (2017.08); *C01B 32/194* (2017.08); *C01B 32/23* (2017.08); *C07D 493/22* (2013.01); *C07F 5/027* (2013.01)

(58) Field of Classification Search
CPC ........................... C07D 493/22; C01B 31/043
USPC ....................................................... 549/543
See application file for complete search history.

(56) References Cited

FOREIGN PATENT DOCUMENTS

| CN | 103663436 A | 3/2014 |
|---|---|---|
| KR | 10-2013-0019169 A | 2/2013 |

OTHER PUBLICATIONS

Gong et al, "Photochemical Synthesis of Fluorinated Graphene Via a Simultaneous Fluorination and Reductions Route", RSC Advances, 2013, 3, p. 6327-6330.
Samanta, Khokan, et al. "Highly hydrophilic and insulating fluorinated reduced graphene oxide." Chemical Communications 49.79 (2013): (11 pages).

*Primary Examiner* — Taylor V Oh
(74) *Attorney, Agent, or Firm* — NSIP Law

(57) ABSTRACT

Functionalized reduced graphene oxide (functionalized rGO), and a method of producing the same are provided. The functionalized reduced graphene oxide comprises reduced graphene oxide which is fluorinated and co-doped with at least one co-dopant selected from the group consisting of B, N and S.

11 Claims, 18 Drawing Sheets

FUNCTIONALIZED REDUCED GRAPHENE OXIDE AND METHODS OF PRODUCING THE SAME

CROSS-REFERENCE TO RELATED APPLICATION

This application is a Divisional of U.S. application Ser. No. 15/263,948, filed on Sep. 13, 2016, which is a Continuation-In-Part Application of U.S. application Ser. No. 14/567,177, filed on Dec. 11, 2014, that claims the benefit under 35 USC 119(a) of Korean Patent Application No. 10-2014-0070860 filed on Jun. 11, 2014, in the Korean Intellectual Property Office, the entire disclosure of which is incorporated herein by reference for all purposes.

BACKGROUND

1. Field

The following description relates to functionalized reduced grapheme oxide (functionalized rGO), a method of preparing the functionalized reduced grapheme oxide (functionalized rGO), graphene compositions including doped and reduced graphene oxide, and methods of preparing the graphene compositions.

2. Description of Related Art

Graphene is a crystalline allotrope of carbon with two-dimensional properties. Other allotropes of carbon include diamond, graphite, carbon nanotube, bukyball, and the like. Graphene comprises a monolayer of carbon atoms arranged within a pattern of repeating honeycomb lattice in two dimensions.

Functionalized graphene has attracted considerable attention. The fictionalization of graphene can alter the chemical, structural and electrical properties of graphene. Various graphene derivatives have been synthesized such as graphene oxide (GO), graphene, different atomic doped GO, and the like. Among the derivatives, GO is one of the most extensively studied forms of functionalized graphene. GO is easily produced by exfoliating oxidized graphite. Recently, the halogenation of graphene provides another possibility for controlling chemical functionalization of graphene as in band-gap engineering. A halogen atom, which is highly electronegative, forms a stronger bond with a carbon atom than a hydrogen atom, producing a more stable graphene derivative composition. This is the principle that enables halogen atoms to accomplish efficient doping and/or band-gap initiation of the graphene. In addition, fluorinated graphene (FG) can promote nerve-guide of stem cells and is used for application of tissue engineering. Accordingly, the synthesis of halogenated graphene is drawing much attention from chemists.

In general, F or Cl plasma, or exposure to $F_2$ at a high temperature has been used to bond F or Cl atoms to a base surface of graphene. Fluorinated graphene can be also obtained from fluorinated graphite by an exfoliating method. However, plasma may cause damage to the graphene by ion bombardment. In addition, the use of a high temperature reaction is not desirable. Decomposition of $XeF_2$ or photochemical decomposition of $Cl_2$ at a certain temperature has been also used for fluorination or chlorination of graphene. An electrochemical process has also been reported with regard to preparation and properties of a single-layer graphene oxyfluoride (OFG). Currently, there are published methods using hydrogen fluoride, which is a corrosive reactant, for fluorination of graphene oxide (GO). In addition, Korean Patent Application Publication No. 10-2013-0019169 describes a method for preparing fluorinated graphene by using expanded graphite. However, an efficient, simple, environment-friendly and solution-based method for synthesis of fluorinated graphene is demanded to test the characteristic of bulk production and actual application.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, functionalized reduced graphene oxide (functionalized rGO), comprising reduced graphene oxide which is fluorinated and co-doped with at least one co-dopant selected from the group consisting of B (boron), N (nitrogen) and S (sulfur).

The reduced graphene oxide may be fluorinated and co-doped with B and N; B and 5; or B, N and S.

The functionalized reduced graphene oxide may be co-doped with the at least one co-dopant includes B and N; B and 5; or B, N and S.

The functionalized reduced graphene oxide may include an amount of F due to the fluorination in a range of from 10 wt % to 40 wt % with respect to the total weight of the functionalized reduced graphene oxide.

The functionalized reduced graphene oxide may include a C/O ratio in the functionalized reduced graphene oxide ranging from 10 to 20.

The functionalized reduced graphene oxide may include an amount of the at least one co-dopant ranging from 0.1 wt % to 10 wt % with respect to the total weight of the functionalized reduced graphene oxide.

The functionalized reduced graphene oxide may have high wettability with a water contact angle of below 90°.

The functionalized reduced graphene oxide may have high resistivity of 2 GΩ or higher.

In another general aspect, a method of producing functionalized reduced graphene oxide, the method involving (a) a step of dispersing a graphene oxide in an organic solvent; and (b) a step of adding $BF_3$-etherate, and at least one co-doping agent selected from the group consisting of alkylthiol, arylthiol, alkylamine and arylamine to the organic solvent in which the graphene oxide is dispersed to produce the functionalized reduced graphene oxide; wherein the functionalized reduced graphene oxide comprises reduced graphene oxide which is fluorinated and co-doped with at least one co-dopant selected from the group consisting of B, N and S.

The step (b) may be carried out at a temperature between about 30° C. to about 150° C.

The organic solvent may include tetrahydrofuran, diethyl ether, or ethyl acetate.

The $BF_3$-etherate may be used as a fluorinating agent and a reducing agent, and the $BF_3$-etherate may be used as a B-doping agent as well.

The alkylthiol, arylthiol, alkylamine, or arylamine as the co-doping agent may be a nucleophile that acts as a sulfur-doping agent or nitrogen-doping agent.

In another general aspect, a method of producing functionalized reduced graphene oxide, the method including reacting graphene oxide with $BF_3$-etherate and at least one co-doping agent selected from a group consisting of alkylthiol, arylthiol, alkylamine, and arylamine in a solvent to produce the functionalized reduced graphene oxide; wherein the functionalized reduced graphene oxide comprises reduced graphene oxide reduced which is fluorinated and co-doped with one or more co-dopants selected from the group consisting of B, N and S.

The reacting of the graphene oxide includes dispersing the graphene oxide in an organic solvent to produce a reaction mixture, and adding the $BF_3$-etherate and the at least co-doping agent selected from the group consisting of alkylthiol, arylthiol, alkylamine, and arylamine to the reaction mixture.

The reacting of the graphene oxide may be performed at a temperature of from about 30° C. to about 150° C.

The general aspect of the method may further involve collecting the produced functionalized reduced graphene oxide by filtering the functionalized reduced graphene oxide from the reaction mixture.

The foregoing summary is illustrative only and is not intended to be in any way limiting. Other features and aspects will be apparent from the following detailed description, the drawings, and the claims.

Figure 1:
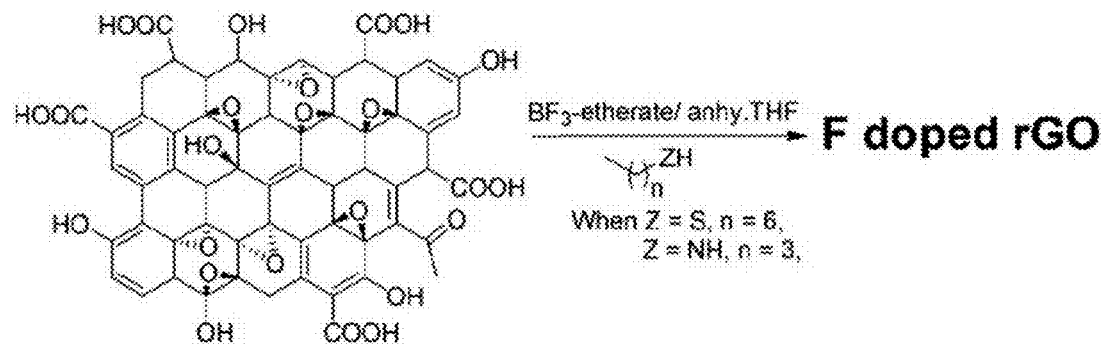
FIG. 1 is a chemical reaction that outlines an example of a method of synthesizing fluorinated-reduced graphene oxide (F-rGO) co-doped by boron and sulfur, or boron and nitrogen by using a $BF_3$-etherate solution and 1-heptanethiol/n-butylamine.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Throughout the disclosure, the phrase "connected to" or "coupled to" are used to designate a connection or coupling of one element to another element and include both an example in which an element is "directly connected or coupled to" another element and an example in which an element is "electronically connected or coupled to" another element via still another element.

Throughout the disclosure, the term "on" that is used to designate a position of one element with respect to another element includes both an example in which the one element is adjacent to the another element and an example in which any other element exists between these two elements.

Throughout the disclosure, the expression "comprises", "includes", "comprising", and/or "including" as used in the disclosure does not exclude one or more other components, steps, operations, or the existence or addition of elements in addition to the described components, steps, operations and/or elements.

Throughout the disclosure, the terms "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party.

Throughout the disclosure, the term "step of does not mean "step for".

Throughout the disclosure, the term "combination of included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the disclosure, the expression" A and/or B" means "A or B, or A and B."

Throughout the disclosure, the term "graphene" means that multiple carbon atoms are bonded to one another through covalent bond, thereby forming polycyclic aromatic molecules, and the carbon atoms bonded through the covalent bond form a six-membered ring as a basic repeat unit, but may further include five- and/or seven-membered rings. Accordingly, a sheet formed of the graphene appears to be a monolayer of the covalently bonded carbon atoms, but may not be limited thereto. The sheet formed of the graphene may have various structures, and the structures may vary depending on a content of the five- and/or seven-membered rings that may be contained in the graphene. Furthermore, if the sheet formed of the graphene is a monolayer, it may be stacked on one another thereby forming multiple layers, and a side end part of the graphene sheet may be saturated with hydrogen atoms, but may not be limited thereto.

Throughout the disclosure, the term "alkyl" may include a linear or branched and saturated or unsaturated $C_{1-7}$, or $C_{1-20}$ alkyl, and for example, may include, but is not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, or possible isomers thereof.

Throughout the disclosure, the term "aryl" used alone or as a part of another group includes a monocyclic or non-cyclic aromatic ring, e.g., phenyl and substituted phenyl, and furthermore, a conjugated group, e.g., naphthyl, phenanthrenyl, indenyl, tetrahydronaphthyl, indanyl. Accordingly, an aryl group may contain one or more ring having five or six or more atoms, there may be five or less rings containing forty-two or less or twenty-two or less atoms, and double bond may be alternatively (resonance) present between neighboring carbon atoms or appropriate heteroatoms. The aryl group may be substituted with at least one group, which includes, but is not limited to, halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2) or thiol.

Hereinafter, examples embodiments have been described in detail, but the present disclosure may not be limited to the example embodiments.

In a first aspect of the present disclosure, there is provided functionalized reduced graphene oxide (functionalized rGO), comprising reduced graphene oxide which is fluorinated and co-doped with at least one co-dopant selected from the group consisting of B (boron), N (nitrogen) and S (sulfur).

In accordance with the example embodiment of the present disclosure, the reduced graphene oxide may be fluorinated and co-doped with B and N; B and 5; or B, N and S, but is not limited thereto.

In accordance with the example embodiment of the present disclosure, the functionalized reduced graphene oxide may include an amount of F due to the fluorination in a range of from about 10 wt % to about 40 wt % with respect to the total weight of the functionalized reduced graphene oxide, but is not limited thereto. For example, the functionalized reduced graphene oxide may include an amount of F due to the fluorination in a range of from about 10 wt % to about 40 wt %, about 15 wt % to about 40 wt %, about 20 wt % to about 40 wt %, about 25 wt % to about 40 wt %, or about 30 wt % to about 40 wt % with respect to the total weight of the functionalized reduced graphene oxide, but is not limited thereto.

In accordance with the example embodiment of the present disclosure, the functionalized reduced graphene oxide may include a C/O ratio in the functionalized reduced graphene oxide, ranging from about 10 to about 20, but is not limited thereto. For example, the functionalized reduced graphene oxide may include the C/O ratio in the functionalized reduced graphene oxide, ranging from about 10 to about 20, about 10 to about 18, about 10 to about 16, about 10 to about 14, about 11 to about 20, about 11 to about 18, about 11 to about 16, about 11 to about 14, about 12 to about 20, about 12 to about 18, about 12 to about 16, or about 12 to about 14, but is not limited thereto.

In accordance with the example embodiment of the present disclosure, the functionalized reduced graphene oxide may include an amount of the at least one co-dopant ranging from about 0.1 wt % to about 10 wt % with respect to the total weight of the functionalized reduced graphene oxide, but is not limited thereto. For example, the functionalized reduced graphene oxide may include an amount of the at least one co-dopant ranging from 0.1 wt % to 10 wt %, 0.1 wt % to 8 wt %, 0.1 wt % to 6 wt %, 0.1 wt % to 4 wt %, 0.1 wt % to 2 wt %, 1 wt % to 10 wt, 1 wt % to 8 wt %, 1 wt % to 6 wt %, 1 wt % to 4 wt %, or 1 wt % to 2 wt % with respect to the total weight of the functionalized reduced graphene oxide, but is not limited thereto.

In accordance with the example embodiment of the present disclosure, the functionalized reduced graphene oxide may have high wettability with a water contact angle of below about 90°, but is not limited thereto. For example, the functionalized reduced graphene oxide may have high wettability with a water contact angle of below about 90°, 80° or less, 80° or less, 70° or less, 60° or less, 50° or less, 40° or less, 30° or less, 20° or less, 10° or less, from 1° to 90°, from 1° to 80°, from 1° to 70°, from 1° to 60°, from 1° to 50°, from 1° to 40°, from 1° to 30°, from 1° to 20°, from 1° to 10°, from 5° to 90°, from 5° to 80°, from 5° to 70°, from 5° to 60°, from 5° to 50°, from 5° to 40°, from 5° to 30°, from 5° to 20°, or from 5° to 10°, but is not limited thereto.

In accordance with the example embodiment of the present disclosure, the functionalized reduced graphene oxide may have high resistivity of about 2 GΩ or higher, but is not limited thereto. For example, the functionalized reduced graphene oxide may have high resistivity of about 2 GΩ or higher, 10 GΩ or higher, 100 GΩ or higher, 200 GΩ or higher, from 2 GΩ to 1,000 GΩ, from 2 GΩ to 900 GΩ, from 2 GΩ to 800 GΩ, from 2 GΩ to 700 GΩ, from 2 GΩ to 600 GΩ, from 2 GΩ to 500 GΩ, from 2 GΩ to 400 GΩ, from 2 GΩ to 300 GΩ, 20 GΩ to 1,000 GΩ, from 20 GΩ to 900 GΩ, from 20 GΩ to 800 GΩ, from 20 GΩ to 700 GΩ, from 20 GΩ to 600 GΩ, from 20 GΩ to 500 GΩ, from 20 GΩ to 400 GΩ, from 20 GΩ to 300 GΩ, 100 GΩ to 1,000 GΩ, from 100 GΩ to 900 GΩ, from 100 GΩ to 800 GΩ, from 100 GΩ to 700 GΩ, from 100 GΩ to 600 GΩ, from 100 GΩ to 500 GΩ, from 100 GΩ to 400 GΩ, or from 100 GΩ to 300 GΩ, but is not limited thereto.

In accordance with an example of the functionalized reduced graphene oxide, maximum fluorination may be as high as about 40 wt %, and the functionalized reduced graphene oxide fluorinated including reduced graphene oxide which is fluorinated and co-doped may have great wettability, high insulating properties, and high wear resistance. In addition, the functionalized reduced graphene oxide fluorinated including reduced graphene oxide which is fluorinated and co-doped has a high insulation property and hydrophilicity, it is promising as a viable platform for tissue-engineering application, and expected to have high cell adhesion and diffusion.

In a second aspect of the present disclosure, there is provided a method of producing functionalized reduced graphene oxide, the method involving (a) a step of dispersing a graphene oxide in an organic solvent; and (b) a step of adding $BF_3$-etherate, and at least one co-doping agent selected from the group consisting of alkylthiol, arylthiol, alkylamine and arylamine to the organic solvent in which the graphene oxide is dispersed to produce the functionalized reduced graphene oxide; wherein the functionalized reduced graphene oxide comprises reduced graphene oxide which is fluorinated and co-doped with at least one co-dopant selected from the group consisting of B, N and S.

In accordance with the example embodiment of the present disclosure, "alkyl" in the alkylthiol or the alkylamine may include saturated or unsaturated and straight- or side-chain alkyl containing $C_{1-20}$, $C_{1-15}$, or $C_{1-10}$, but is not limited thereto.

In accordance with the example embodiment of the present disclosure, "aryl" in the arylthiol or the arylamine may have $C_6$ to $C_{42}$, and include, but is not limited to, a monocyclic or non-cyclic aromatic ring, e.g., phenyl and substituted phenyl, and furthermore, a conjugated group, e.g., naphthyl, phenanthrenyl, indenyl, tetrahydronaphthyl, or indanyl. In addition, the aryl may be induced from naphthalene, anthracene, pyrene, coronene, rubrene, a graphene quantum dot, or graphene.

In accordance with the example embodiment of the present disclosure, the graphene oxide in the above step (a) may have a functional group selected from the group consisting of a large amount of an epoxide group, a hydroxyl group, a carboxyl group, a ketone group and combinations thereof, but is not limited thereto.

In accordance with the example embodiment of the present disclosure, the reduced graphene oxide may be co-doped by at least one element selected from the group consisting of boron, sulfur, nitrogen and combinations thereof in the step (b), in addition to fluorine, but is not limited thereto.

In accordance with the example embodiment of the present disclosure, the step (b) may be carried out under a nitrogen atmosphere, but is not limited thereto.

In accordance with the example embodiment of the present disclosure, the step (b) may be carried out at a temperature of from about 30° C. to about 150° C., but is not limited thereto. For example, the temperature may be from about 30° C. to about 40° C., from about 30° C. to about 50° C., from about 30° C. to about 60° C., from about 30° C. to about 70° C., from about 30° C. to about 80° C., from about 30° C. to about 90° C., from about 30° C. to about 100° C., from about 30° C. to about 110° C., from about 30° C. to about 120° C., from about 30° C. to about 130° C., from about 30° C. to about 140° C., from about 30° C. to about 150° C., from about 40° C. to about 50° C., from about 40° C. to about 60° C., from about 40° C. to about 70° C., from about 40° C. to about 80° C., from about 40° C. to about 90° C., from about 40° C. to about 100° C., from about 40° C. to about 110° C., from about 40° C. to about 120° C., from about 40° C. to about 130° C., from about 40° C. to about 140° C., from about 40° C. to about 150° C., from about 50° C. to about 60° C., from about 50° C. to about 70° C., from about 50° C. to about 80° C., from about 50° C. to about 90° C., from about 50° C. to about 100° C., from about 50° C. to about 110° C., from about 50° C. to about 120° C., from about 50° C. to about 130° C., from about 50° C. to about 140° C., from about 50° C. to about 150° C., from about 60° C. to about 70° C., from about 60° C. to about 80° C., from about 60° C. to about 90° C., from about 60° C. to about 100° C., from about 60° C. to about 110° C., from about 60° C. to about 120° C., from about 60° C. to about 130° C., from about 60° C. to about 140° C., from about 60° C. to about 150° C., from about 70° C. to about 80° C., from about 70° C. to about 90° C., from about 70° C. to about 100° C., from about 70° C. to about 110° C., from about 70° C. to about 120° C., from about 70° C. to about 130° C., from about 70° C. to about 140° C., from about 70° C. to about 150° C., from about 80° C. to about 90° C., from about 80° C. to about 100° C., from about 80° C. to about 110° C., from about 80° C. to about 120° C., from about 80° C. to about 130° C., from about 80° C. to about 140° C., from about 80° C. to about 150° C., from about 90° C. to about 100° C., from about 90° C. to about 110° C., from about 90° C. to about 120° C., from about 90° C. to about 130° C., from about 90° C. to about 140° C., from about 90° C. to about 150° C., from about 100° C. to about 110° C., from about 100° C. to about 120° C., from about 100° C. to about 130° C., from about 100° C. to about 140° C., from about 100° C. to about 150° C., from about 110° C. to about 120° C., from about 110° C. to about 130° C., from about 110° C. to about 140° C., from about 110° C. to about 150° C., from about 120° C. to about 130° C., from about 120° C. to about 140° C., from about 120° C. to about 150° C., from about 130° C. to about 140° C., from about 130° C. to about 150° C., or from about 140° C. to about 150° C., but is not limited thereto.

In accordance with the example embodiment of the present disclosure, the organic solvent may include tetrahydrofuran (THF), diethyl ether, or ethyl acetate, but is not limited thereto.

In accordance with the example embodiment of the present disclosure, the $BF_3$-etherate may be used as a fluorinating agent and a reducing agent, but is not limited thereto. For example, the $BF_3$-etherate may be in a form of anhydrous BF$_3$-etherate solution, but is not limited thereto. Further, the BF$_3$-etherate may be used as a B-doping agent as well.

In accordance with the example embodiment of the present disclosure, the co-doping agent includes at least one of alkylthiol and arylthiol with at least one of alkylamine and arylamine, but is not limited thereto.

In accordance with the example embodiment of the present disclosure, the alkylthiol, the arylthiol, the alkylamine, or the arylamine may have nucleophilicity and may act as a sulfur- or nitrogen-doping agent, but is not limited thereto. For example, the alkylthiol may be selected from the group consisting of methanethiol, ethanethiol, propanethiol, butanethiol, pentanethiol, hexanethiol, heptanethiol, octanethiol, nonanethiol, decanethiol, undecanethiol, and combinations thereof, but is not limited thereto. In addition, for example, the alkylamine may be selected from the group consisting of methylamine, ethylamine, propylamine, butylamine, pentylamine, hexylamine, heptylamine, octylamine, nonylamine, decylamine, undecylamine, and combinations thereof, but is not limited thereto.

In accordance with the example embodiment of the present disclosure, the alkylthiol or the arylthiol may include S—B bond causing generation of high fluorine ions, but is not limited thereto.

In accordance with the example embodiment of the present disclosure, the alkylamine or the arylamine may include N—B bond causing generation of high fluorine ions, but is not limited thereto.

In accordance with the example embodiment of the present disclosure, the reduced graphene oxide may be fluorinated and co-doped with B and N; B and S; or B, N and S, but is not limited thereto.

In accordance with the example embodiment of the present disclosure, the functionalized reduced graphene oxide may include an amount of F due to the fluorination in a range of from 10 wt % to 40 wt % with respect to the total weight of the functionalized reduced graphene oxide, but is not limited thereto. For example, the functionalized reduced graphene oxide may include an amount of F due to the fluorination in a range of from 10 wt % to 40 wt %, 15 wt % to 40 wt %, 20 wt % to 40 wt %, 25 wt % to 40 wt %, or 30 wt % to 40 wt % with respect to the total weight of the functionalized reduced graphene oxide, but is not limited thereto.

In accordance with the example embodiment of the present disclosure, the functionalized reduced graphene oxide may include a C/O ratio in the functionalized reduced graphene oxide ranging from about 10 to 20, but is not limited thereto. For example, the functionalized reduced graphene oxide may include the C/O ratio in the functionalized reduced graphene oxide, ranging from about 10 to about 20, 10 to 18, 10 to 16, 10 to 14, 11 to 20, 11 to 18, 11 to 16, 11 to 14, 12 to 20, 12 to 18, 12 to 16, or 12 to 14, but is not limited thereto.

In accordance with the example embodiment of the present disclosure, the functionalized reduced graphene oxide may include an amount of the at least one co-dopant ranging from about 0.1 wt % to about 10 wt % with respect to the total weight of the functionalized reduced graphene oxide, but is not limited thereto. For example, the functionalized reduced graphene oxide may include an amount of the at least one co-dopant ranging from 0.1 wt % to 10 wt %, 0.1 wt % to 8 wt %, 0.1 wt % to 6 wt %, 0.1 wt % to 4 wt %, 0.1 wt % to 2 wt %, 1 wt % to 10 wt, 1 wt % to 8 wt %, 1 wt % to 6 wt %, 1 wt % to 4 wt %, or 1 wt % to 2 wt % with respect to the total weight of the functionalized reduced graphene oxide, but is not limited thereto.

In accordance with the example embodiment of the present disclosure, the functionalized reduced graphene oxide may have high wettability with a water contact angle of below about 90°, but is not limited thereto. For example, the functionalized reduced graphene oxide may have high wettability with a water contact angle of below about 90°, 80° or less, 80° or less, 70° or less, 60° or less, 50° or less, 40° or less, 30° or less, 20° or less, 10° or less, from 1° to 90°, from 1° to 80°, from 1° to 70°, from 1° to 60°, from 1° to 50°, from 1° to 40°, from 1° to 30°, from 1° to 20°, from 1° to 10°, from 5° to 90°, from 5° to 80°, from 5° to 70°, from 5° to 60°, from 5° to 50°, from 5° to 40°, from 5° to 30°, from 5° to 20°, or from 5° to 10°, but is not limited thereto.

In accordance with the example embodiment of the present disclosure, the functionalized reduced graphene oxide may have high resistivity of about 2 GΩ or higher, but is not limited thereto. For example, the functionalized reduced graphene oxide may have high resistivity of about 2 GΩ or higher, 10 GΩ or higher, 100 GΩ or higher, 200 GΩ or higher, from 2 GΩ to 1,000 GΩ, from 2 GΩ to 900 GΩ, from 2 GΩ to 800 GΩ, from 2 GΩ to 700 GΩ, from 2 GΩ to 600 GΩ, from 2 GΩ to 500 GΩ, from 2 GΩ to 400 GΩ, from 2 GΩ to 300 GΩ, 20 GΩ to 1,000 GΩ, from 20 GΩ to 900 GΩ, from 20 GΩ to 800 GΩ, from 20 GΩ to 700 GΩ, from 20 GΩ to 600 GΩ, from 20 GΩ to 500 GΩ, from 20 GΩ to 400 GΩ, from 20 GΩ to 300 GΩ, 100 GΩ to 1,000 GΩ, from 100 GΩ to 900 GΩ, from 100 GΩ to 800 GΩ, from 100 GΩ to 700 GΩ, from 100 GΩ to 600 GΩ, from 100 GΩ to 500 GΩ, from 100 GΩ to 400 GΩ, or from 100 GΩ to 300 GΩ, but is not limited thereto.

In another aspect of the present disclosure, there is a method of producing functionalized reduced graphene oxide, the method including reacting graphene oxide with BF$_3$-etherate and at least one co-doping agent selected from a group consisting of alkylthiol, arylthiol, alkylamine, and arylamine in a solvent to produce the functionalized reduced graphene oxide; wherein the functionalized reduced graphene oxide comprises reduced graphene oxide reduced which is fluorinated and co-doped with one or more co-dopants selected from the group consisting of B, N and S.

In accordance with the example embodiment of the present disclosure, the reacting of the graphene oxide includes dispersing the graphene oxide in an organic solvent to produce a reaction mixture, and adding the BF$_3$-etherate and the at least co-doping agent selected from the group consisting of alkylthiol, arylthiol, alkylamine, and arylamine to the reaction mixture.

In accordance with an example of the method of the functionalized reduced graphene oxide, a convenient method for synthesizing a highly-fluorinated and co-doped reduced graphene oxide from graphene oxide using a BF$_3$-etherate solution and alkylthiol, arylthiol, alkylamine or arylamine in a gram scale may be provided by using a detailed mechanism. In accordance with an example of a method of synthesizing the functionalized reduced graphene oxide, maximum fluorination may be as high as about 40 wt %, and the functionalized reduced graphene oxide may have great wettability, high insulating properties, and high wear resistance. In accordance with an example of a method of synthesizing the functionalized reduced graphene oxide, a bulk F-doped and co-doped rGO may be prepared in a large scale for electrical application like a memory property, a high dielectric constant and others, and this is believed to be the first attempt for fluorination of GO using BF$_3$-etherate as a fluorine source. In addition, since the functionalized reduced graphene oxide has a high insulation property and hydrophilicity, the functionalized reduced graphene oxide is promising as a viable platform for tissue-engineering application, and expected to have high cell adhesion and diffusion.

Hereinafter, example embodiments will be described more in detail by using Examples, but the Examples are merely illustrative to facilitate understanding of the present disclosure, and the present disclosure is not limited to the Examples.

EXAMPLES

Pure graphite (Bay Carbon, SP-1 graphite), sulfuric acid (95% to 97%), hydrogen peroxide (30 wt %), potassium permanganate, sodium nitrate, $BF_3$-etherate, 1-heptanethiol, and n-butylamine were obtained and used from common sources.

Graphene oxide (GO) was prepared from natural graphite powders by a modified Hummers and Offeman method using sulfuric acid, potassium permanganate, and sodium nitrate.

The GO (200 mg) prepared by the above-described method was dispersed in 100 mL dry tetrahydrofurane (THF), and a $BF_3$-etherate solution and 1-heptanethiol/n-butylamine were added thereto under a $N_2$ atmosphere. Subsequently, the temperature was increased to 60° C., and the reaction was carried out for 24 hours. Subsequently, the reaction mixture was filtered and washed first with THF to remove an excessive amount of the $BF_3$-etherate and the 1-heptanethiol/n-butylamine, and thereafter, washed several times by using deionized water to remove a by-product formed during the reaction. Subsequently, the reactant was dried at 60° C. under vacuum so that fluorinated-reduced graphene oxide (F-rGO) was prepared.

<Characterization>

Raman spectroscopy measurement was conducted by using 2.41 eV (514 nm) excitation energy and a micro-Raman system (Renishaw, RM1000-In Via). All X-ray photoemission spectroscopy (XPS) measurements were conducted at 100 W by an Al-Kα X-ray source and SIGMA PROBE (ThermoVG, U.K.). FT-IR spectra were collected by using the Thermo Nicolet AVATAR 320 device. Microstructures were observed by a field emission scanning electron microscope (FE-SEM; JSM-6701F/INCA Energy, JEOL). A thermal property of the rGO was analyzed by TGA (Polymer Laboratories, TGA 1000 plus). All UV-vis absorption spectra were recorded by using a double-beam UV-1650PC spectrophotometer (Shimadzu).

With respect to conventional fluorination of graphene oxide (GO), there are methods using hydrogen fluoride, which is a corrosive reactant, and others, and Table 1 below compares the conventional methods and the method in accordance with example embodiments.

TABLE 1

| Journals | Starting Materials | Methods | F-coverage | Remarks |
|---|---|---|---|---|
| Small 2010, 6, 2877-2884 | i) Graphite fluoride ii) Graphene and $XeF_2$ | i) Mechanical cleavage ii) Exposure of atomic fluorine | They prepared Fluorographene (fully fluorinated graphene) and also partially fluorinated graphene. | Atomic exposure is high energy process |
| RSC Adv. 2012, 6, 2877-2884 | Graphite fluoride | Exfoliation by Arc discharge | 10% fluorine coverage | Arc discharge is not suitable. |
| RSC Adv. 2013, 3, 6327-6330 | Graphene oxide and HF | UV irradiation | 50% fluorine coverage | HF is highly corrosive reagent |
| RSC Adv. 2013, 3, 3881-3884 | Graphene oxide and HF | Using nickel tube | Not mentioned (It is cleared from XPS that F-coverage is very low) | HF is highly corrosive |
| Nano letters 2010, 10, 3001-3005 | Graphene | Exposure of $XeF_2$ gas | 25% F-coverage | Not convenient |
| Nano letters 2012, 12, 2374-2378 | Graphene and fluoropolymer | Laser irradiation | $C_nF$, n > 1 i.e. not fluorographene | Not convenient |
| Method of the present disclosure | Graphene oxide and $BF_3$ (as a fluorinating agent) | Simply solution-based method | ~67% F-coverage | More convenient, solution based and more greener way |

In the present Example, the inventors of the present disclosure adopted a very easy solution-based method for synthesizing a greatly large amount of fluorinated reduced graphene oxide (F-rGO) from GO by using anhydrous $BF_3$-etherate and alkylthiol/alkylamine in a gram scale (FIG. 1), and inspected high hydrophilicity (FIG. 3D) and an insulation property (FIG. 9A) of the fluorinated reduced graphene oxide. In this regard, the inventors of the present disclosure optimized the reaction condition based on XPS, and summarized the inspection results in Table 2 as follows:

TABLE 2

| Entry No. | $BF_3$ (mL) | A (mL) | Temp (° C.) | wt % of F | Other Elements | C/O |
|---|---|---|---|---|---|---|
| 1 | 6 | 1 | 60 | 20.0 | B = 3.2 S = 2.6 | 13.8 |
| 2 | 6 | 0 | 60 | 1.4 | B = 0.6 | 20.4 |
| 3 | 6 | 0 | r.t. | 1.6 | B = 2.1 | 2.6 |
| 4 | 0 | 1 | 60 | 0.0 | S = 2.0 | 3.1 |
| 5 | 6 | 1 | r.t. | 2.7 | B = 0.6 S = 2.7 | 11.5 |
| 6 | 3 | 0.5 | 60 | 4.3 | B = 1.1 S = 2.7 | 13.2 |
| 7 | 6 | 0.5 | 60 | 4.7 | B = 1.1 S = 2.6 | 13.6 |

TABLE 2-continued

| Entry No. | $BF_3$ (mL) | A (mL) | Temp (° C.) | wt % of F | Other Elements | C/O |
|---|---|---|---|---|---|---|
| 8 | 12 | 2 | 60 | 19.3 | B = 3.2<br>S = 2.7 | 13.5 |
| 9 | 6 | 1 | 60 | 38.0 | B = 6.1<br>N = 7.9 | 11.7 |

(In Table 2, "$BF_3$" refers to a $BF_3$-etherate solution, "A" of Entry Nos. 1 to 8 refers to 1-heptanethiol, "A" of Entry No. 9 refers to n-butylamine, and "other Elements" are based on wt %).

Figure 4:
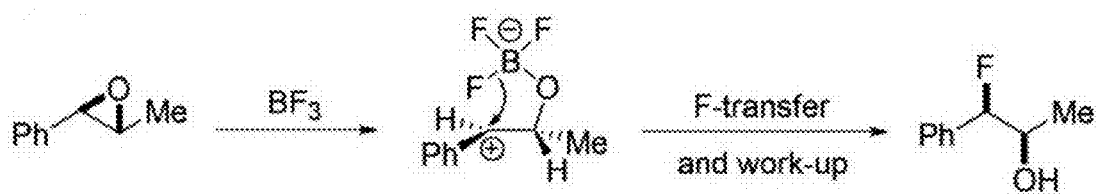
FIG. 4 is a chemical reaction illustrating a presumed mechanism for $BF_3$-etherate and ring-opening hydrogen fluorination according to an example of a method of synthesizing functionalized graphene.
Figure 5:
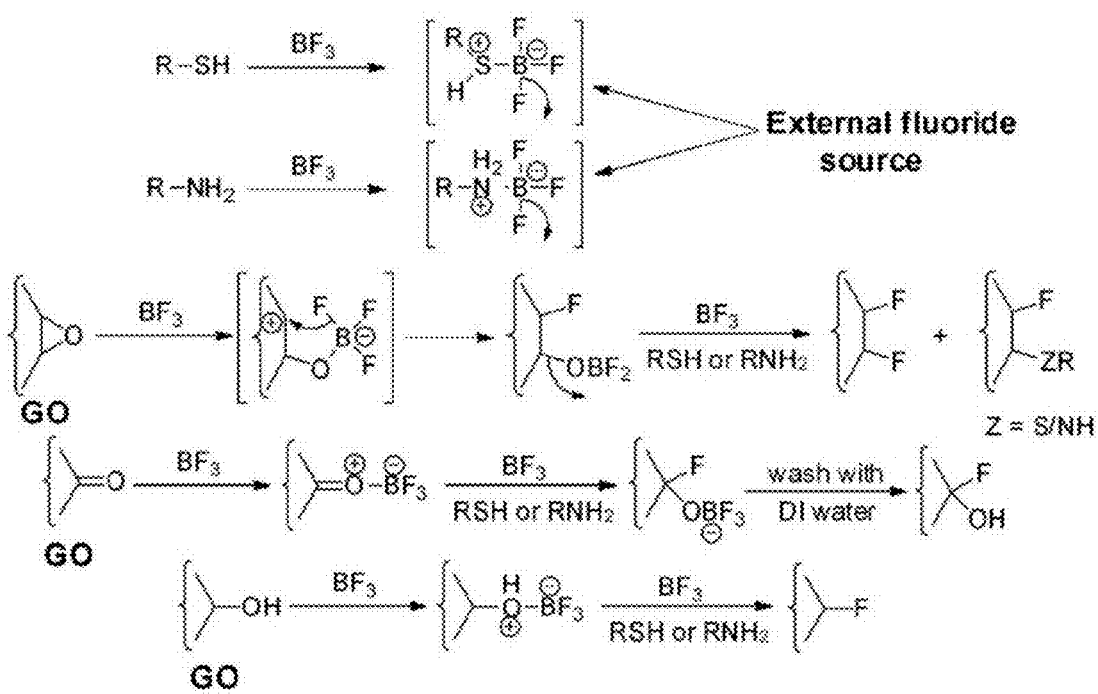
FIG. 5 includes chemical reactions that illustrate presumed mechanisms for fluorination of GO using $BF_3$-etherate and 1-hepthanethiol/n-butylamine according to examples of methods of synthesizing functionalized graphene.
Figure 6:
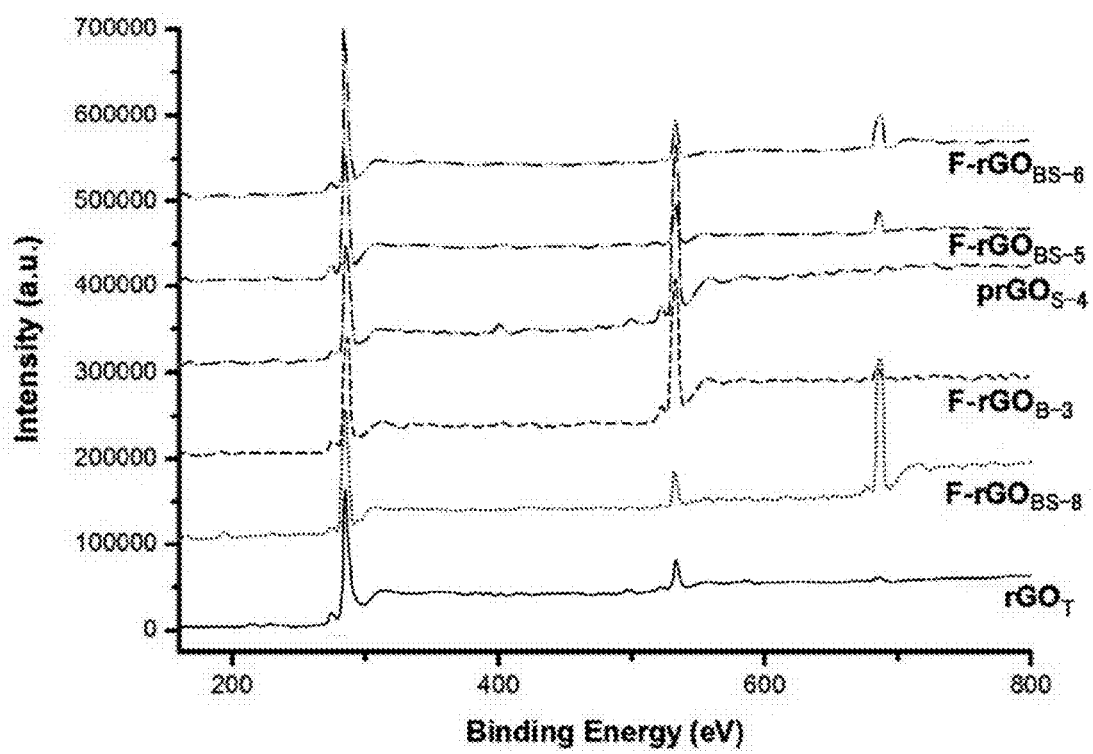
FIG. 6 is a graph that illustrates XPS spectra of F-doped reduced GOs, like rGO$_T$, F-rGO$_{BS-8}$ (Entry No. 8 of Table 2), F-rGO$_{B-3}$ (Entry No. 3 of Table 2), prGO$_{S-4}$ (Entry No. 4 of Table 2), F-rGO$_{BS-5}$ (Entry No. 5 of Table 2), and F-rGO$_{BS-6}$ (Entry No. 6 of Table 2), which have been prepared by reaction of GO with a $BF_3$-etherate solution and 1-heptanethiol/n-butylamine in different conditions.

The GO (200 mg) dispersed in dry THF (100 mL) was treated by $BF_3$-etherate (6 mL) and 1-heptanethiol (1 mL) at 60° C. under a $N_2$ atmosphere so that fluorinated (20 wt %) rGO was prepared together with a small amount of boron and sulfur (Entry No. 1 of Table 2, F-rGO$_{BS-4}$). For understanding of the mechanism and the above-described purpose of the optimization, the present Example diversified the reactants and the reaction conditions (refer to Table 2 for comparison of details), and provided the optimum condition as described in Entry No. 1 of Table 2. For easier understanding of the fluorination mechanism, 1-heptanethiol was replaced with n-butylamine, and 38 wt % fluorinated rGO co-doped by nitrogen and boron (Entry No. 9 of Table 2, F-rGO$_{BN-1}$) was obtained according to expectation of the inventors of the present disclosure. When the inventors of the present disclosure carried out the reaction with $BF_3$-etherate and alkylthiol, which were doubled in an amount (Entry No. 8 of Table 2), the same result as obtained in Entry No. 1 of Table 2 was achieved (FIG. 6, Entry No. 8 of Table 2, F-rGO$_{BS-8}$). Presumed mechanism to enable the fluorination of the GO is provided in FIG. 4. In case of the present Example, the GO sheets obtained included a large amount of epoxide functional groups, hydroxy functional groups, carboxyl functional groups, and ketone functional groups. Of the functional groups, the epoxide functional group could be subject to coordinate bond to $BF_3$-etherate, and generate fluorine ions according to the above-described mechanism, so that fluorination in molecules could easily occur. Further, the fluorine ions within the molecules were also prepared by the reaction of $BF_3$-ethereate and alkylthiol/alkylamine according to the mechanism discussed in FIG. 5. In addition, there is a possibility that the fluorine ions will be generated by the coordinate bond of alcohol of GO and the ketone functional group to $BF_3$-etherate (FIG. 5). Accordingly, the prepared fluorine ions caused the fluorination reaction in the GO, resulting in the production of a large amount of F-doped rGO. After studying the results of the reactions summarized in Table 2, it was clearly confirmed that, when $BF_3$-etherate was used alone, a lower degree of fluorination occurred. Surprisingly, when $BF_3$-etherate and alkylthiol/alkylamine were used together, a higher degree of fluorination occurred. Accordingly, it has been demonstrated that, in the present Example, $BF_3$ acted as a fluorine source, and alkylthiol or alkylamine acted as an activator promoting the generation of a great number of fluorine ions by allowing the formation of coordinate bonds to the $BF_3$. As alkylamine or arylamine has higher basicity (Lewis base) than alkylthiol or arylthiol, the alkylamine forms a stronger ionic N—B bond with $BF_3$ (Lewis acid) than the B—F coordinate bonds of $BF_3$ (Lewis acid), which causes the generation of more free fluorine ions, and thereby, causing a higher rate of fluorination and is stronger than S—B bond (Table 2) to be consistent with the results of the present Example. As the alkylthiol and the alkylamine may also act as a nucleophile, the sulfur or the nitrogen could also be doped simultaneously with fluorine (FIG. 5). The generation of the fluorine ions was higher at 60° C., which is higher than 0° C., and this caused a higher rate of fluorination (Table 2).

Figure 2A:
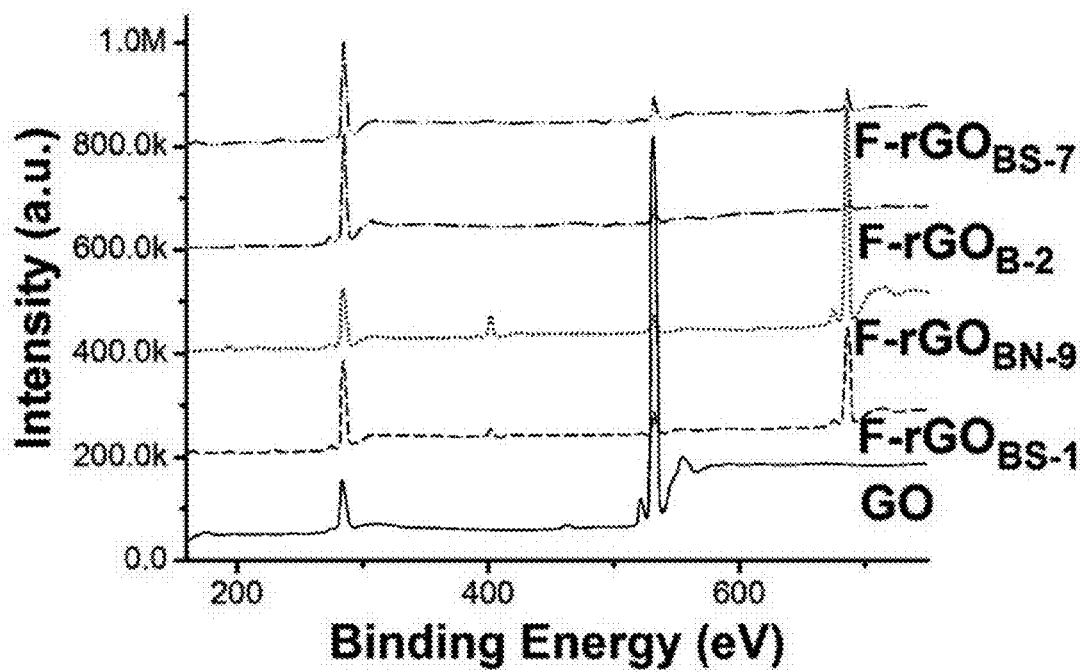
FIG. 2A is a graph that illustrates XPS spectra of different F-doped rGOs according to a number of examples of methods of synthesizing functionalized graphene.
Figure 2B:
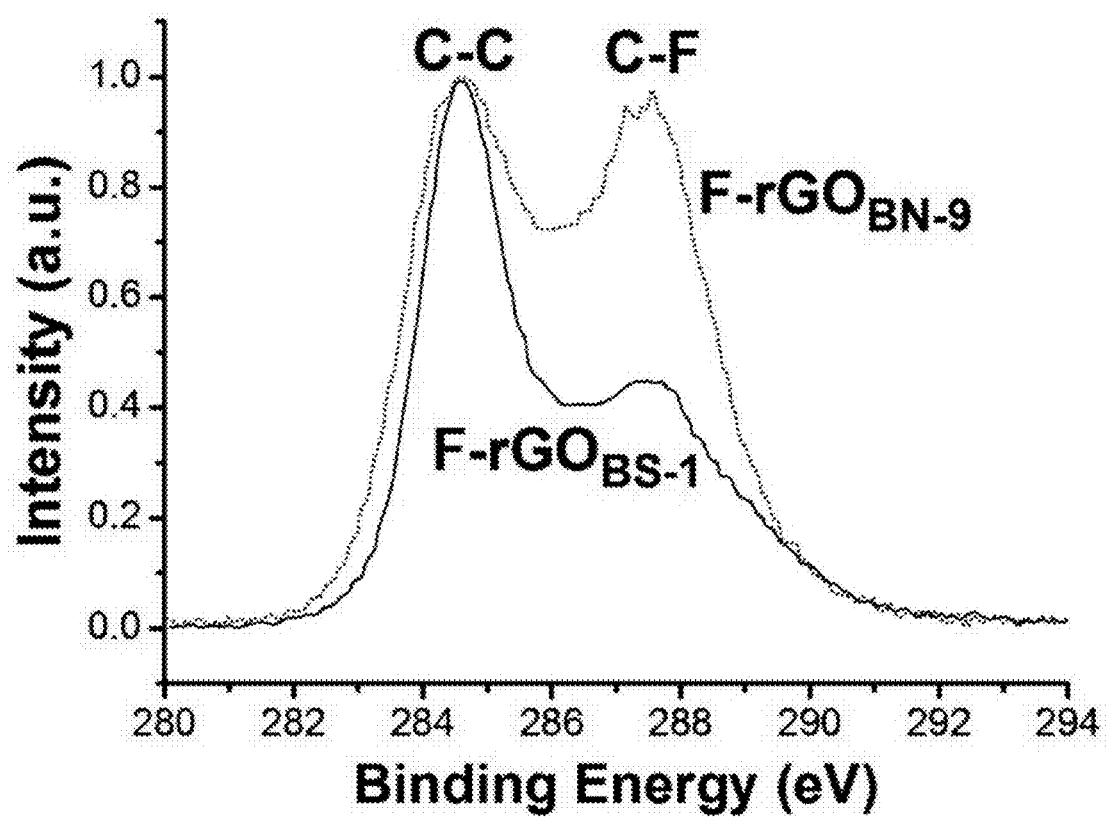
FIG. 2B is a graph that illustrates high-resolution C 1s spectra of F-rGO$_{BS-1}$ (Entry No. 1 of Table 2) and F-rGO$_{BN-9}$ (Entry No. 9 of Table 2) according to a number of examples of methods of synthesizing functionalized graphene.
Figure 2C:
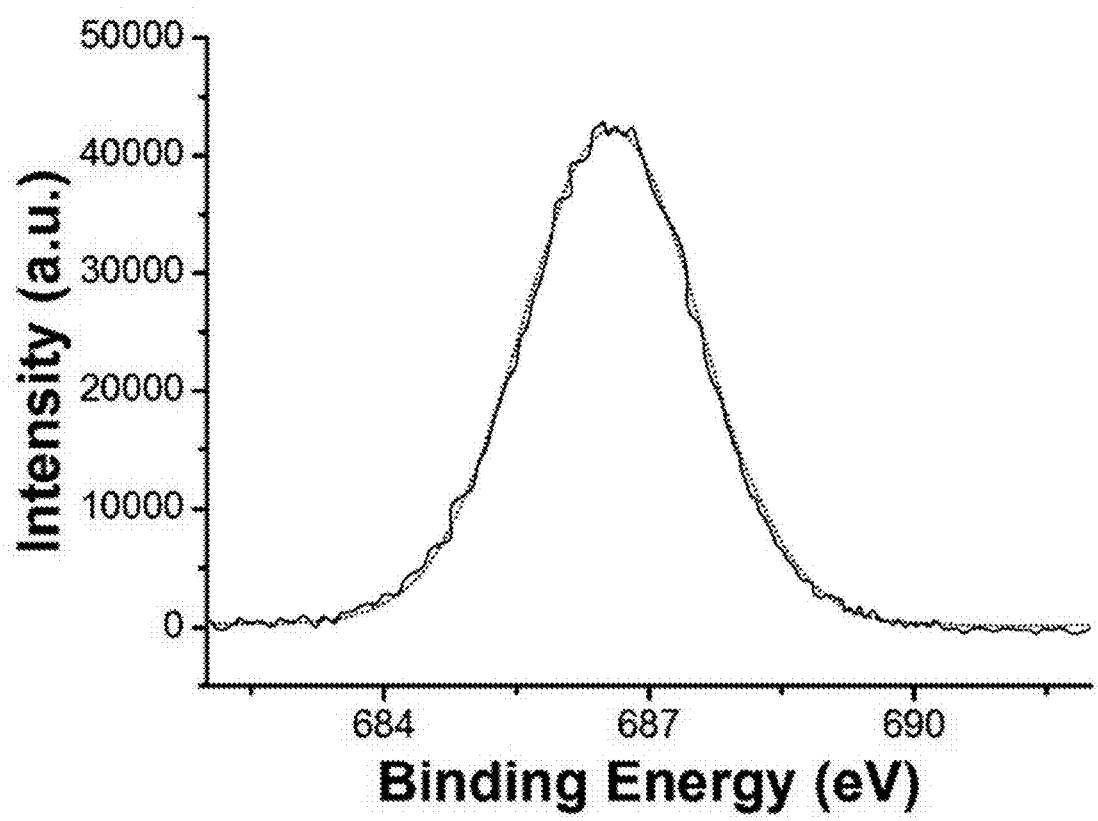
FIG. 2C is a graph that illustrates high-resolution F 1s spectra of F-rGO$_{BN-9}$ according to an example of a method of synthesizing functionalized graphene.
Figure 2D:
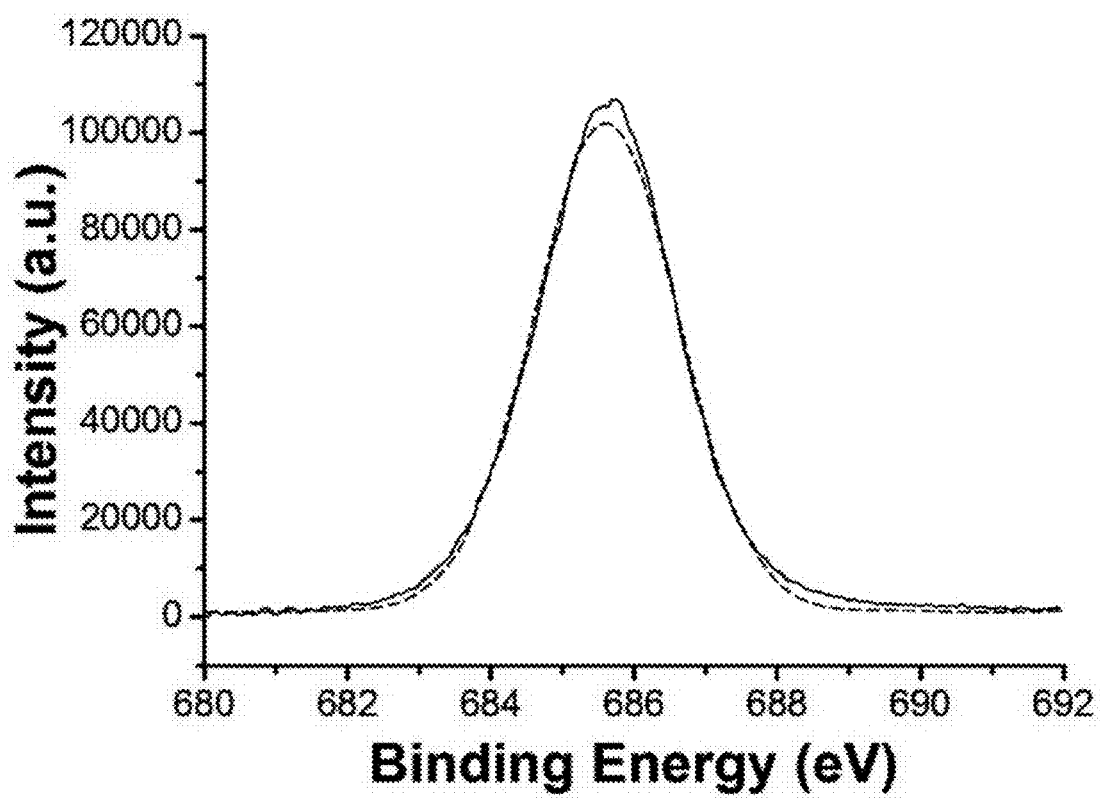
FIG. 2D is a graph that illustrates high-resolution F 1s spectra of F-rGO$_{BS-1}$ according to an example of a method of synthesizing functionalized graphene.
Figure 7:
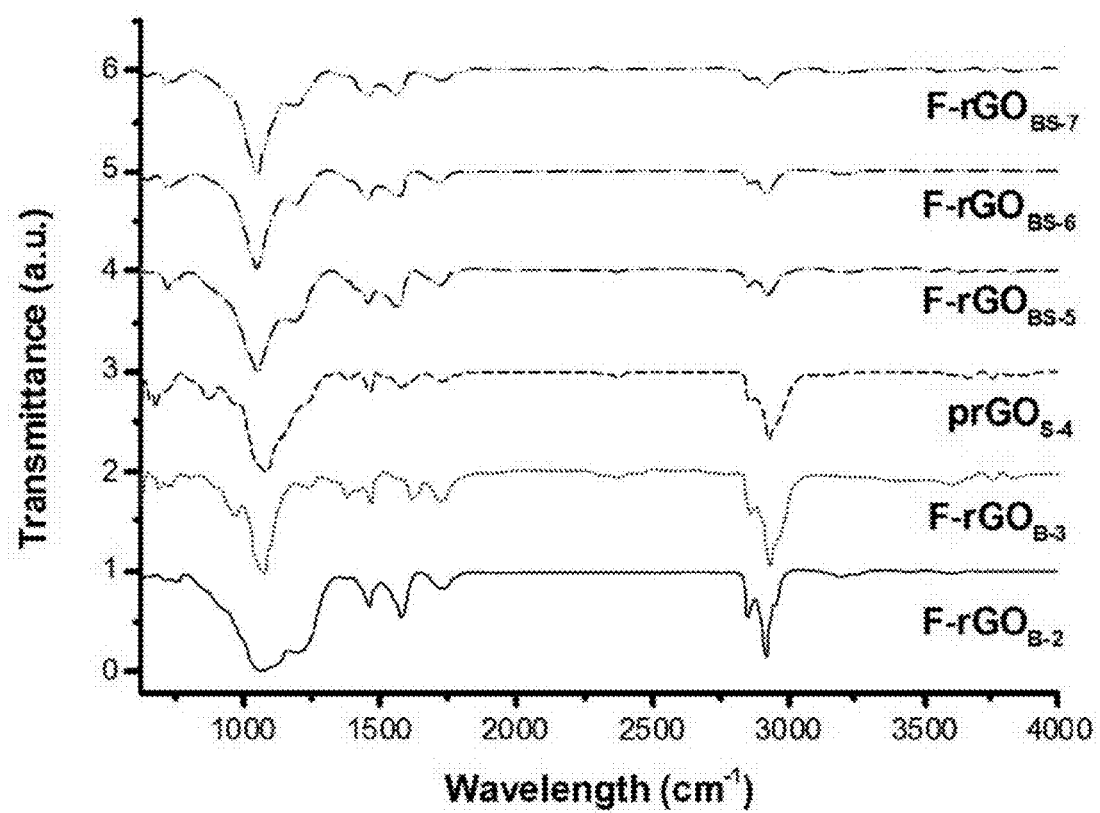
FIG. 7 is a graph that illustrates FT-IR spectra of F-doped rGOs, like F-rGO$_{B-2}$, F-rGO$_{B-3}$, prGO$_{S-4}$, F-rGO$_{BS-6}$, F-rGO$_{BS-6}$, and F-rGO$_{BS-7}$ (Entry No. 7 of Table 2), which have been prepared by reaction of GO with a $BF_3$-etherate solution and 1-heptanethiol/n-butylamine in different conditions.
Figure 8:
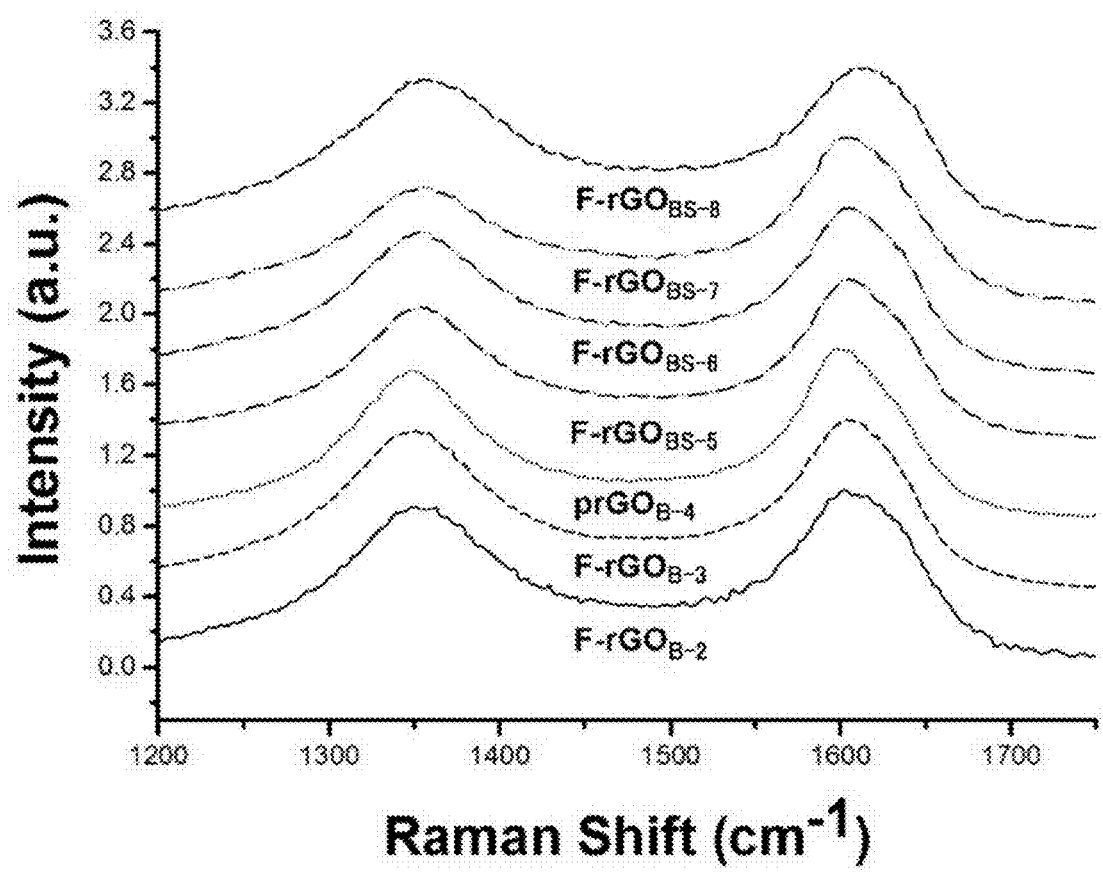
FIG. 8 is a graph that illustrates Raman spectra of F-doped reduced GOs, like F-rGO$_{B-2}$, F-rGO$_{B-3}$, prGO$_{S-4}$, F-rGO$_{BS-5}$, F-rGO$_{BS-6}$, F-rGO$_{BS-7}$, and F-rGO$_{BS-8}$, which have been prepared by reaction of GO with a $BF_3$-etherate solution and 1-heptanthiol/n-butylamine in different conditions.

The mixture of the fluorine component in the F-rGO prepared in the present Example was characterized by using X-ray photoelectron spectroscopy (XPS). FIGS. 2A to 2D and FIG. 6 show comparison of XPS spectra under different reaction conditions. Variations in the fluorine amounts depending on the reaction conditions were listed in Table 2. FIGS. 2B, 2C, and 2D show typical C 1s and F 1s XPS spectra for F-rGO$_{BS-1}$ and F-rGO$_{BN-9}$. F-rGO$_{BS-1}$ and F-rGO$_{BN-9}$ were calculated to have contained about 20 wt % F and 30 wt % F, respectively. A peak of C═C bond appearing at 284.6 eV was prevailing in both the samples of F-rGO$_{BS-4}$ and F-rGO$_{BN-1}$. The peak centered at 287.6 eV (FIG. 2B) is attributed to semi-ionic C—F bond. In addition, as shown in FIGS. 2A to 2D, a clear F 1s core level peak (FIG. 2D) appeared at 685.9 eV for the F-rGO$_{BS-1}$ sample, and a F 1s core level peak for the F-rGO$_{BN-9}$ sample appeared at 686.6 eV (FIG. 2C). From the XPS spectra, a C/O ratio was 13.8 for F-rGO$_{BS-1}$ and 11.7 for F-rGO$_{BN-9}$ (Table 2), which imply higher quality reduction than $NaBH_4$, concentrated $H_2SO_4$, reduced GO (a C/O ratio of 8.57), and hydrazine-reduced GO (a C/O ratio of 10.3) in this order. When the inventors of the present disclosure used only $BF_3$-etherate at a temperature of 60° C., the high quality reduction occurred by using 1.4% fluorination (Entry No. 2 of Table 2, F-rGO$_{B-2}$) (a C/O ratio of 20.4). Fourier transform infrared spectroscopy (FT-IR) was further used for study of the fluorination and the reduction process by the above-described reaction (FIG. 3A and FIG. 7).

Figure 3A:
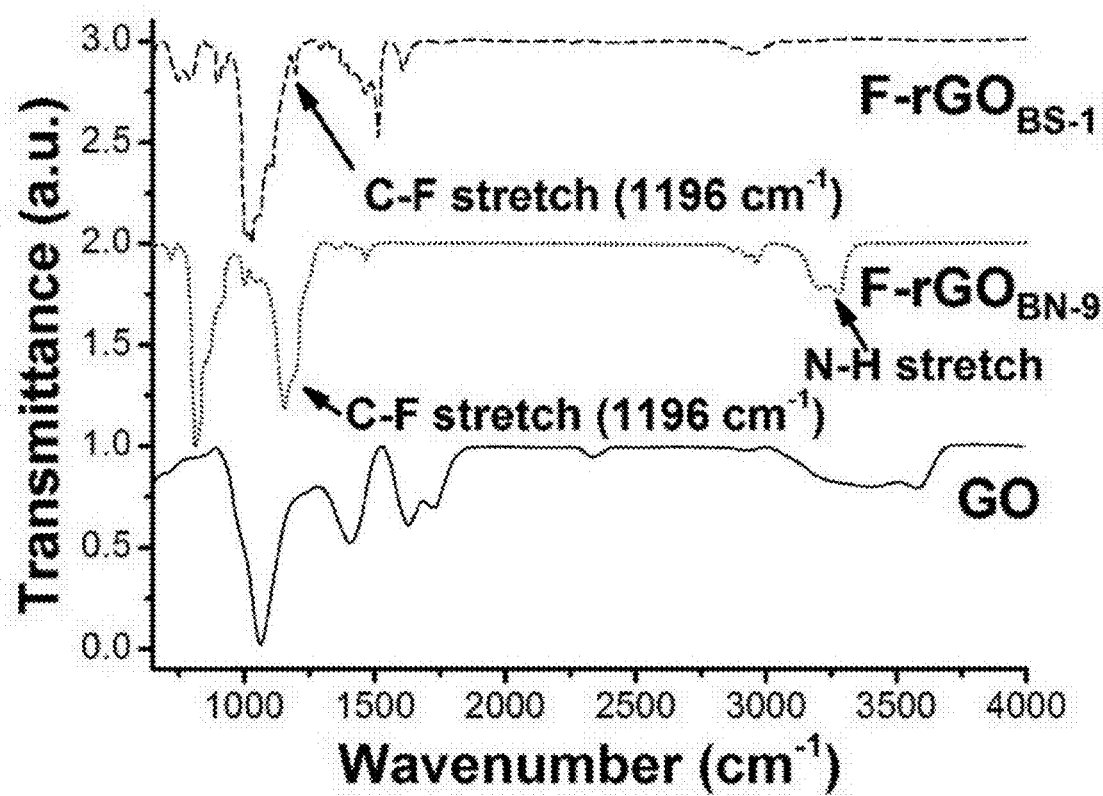
FIG. 3A is a graph that illustrates FT-IR spectra of GO, F-rGO$_{BN-9}$, and F-rGO$_{BS-1}$ according to a number of examples of methods of synthesizing functionalized graphene.

The characteristic peaks in the IR spectra of the GO were ~3,409 cm$^{-1}$ (broad, O—H stretching), 2,948 cm$^{-1}$, ($CH_2$, stretching), 1,728 cm$^{-1}$ (C═O stretching), 1,632 cm$^{-1}$ (C═C stretching), 1,404 cm$^{-1}$ (O—H bending), and 1,065 cm$^{-1}$ (C—O—C stretching from an epoxide group and/or an ester group) (FIG. 3A). In the IR spectra of F-rGO$_{BS-1}$ and FrGO$_{BN-9}$, no peaks appeared at 1,728 cm$^{-1}$, 1,404 cm$^{-1}$ and 1,065 cm$^{-1}$; while significantly low intensity was exhibited at 3,409 cm$^{-1}$, a new peak occurred at 1,196 cm$^{-1}$ (C—F stretching); bond of fluorine atoms, —COOH, >C═O, and the epoxide functional group were absent; and a —OH group was reduced. IR spectra of other compounds were provided in FIG. 7. This measurement was effective verification for the fluorination and the in-situ reduction.

Figure 3B:
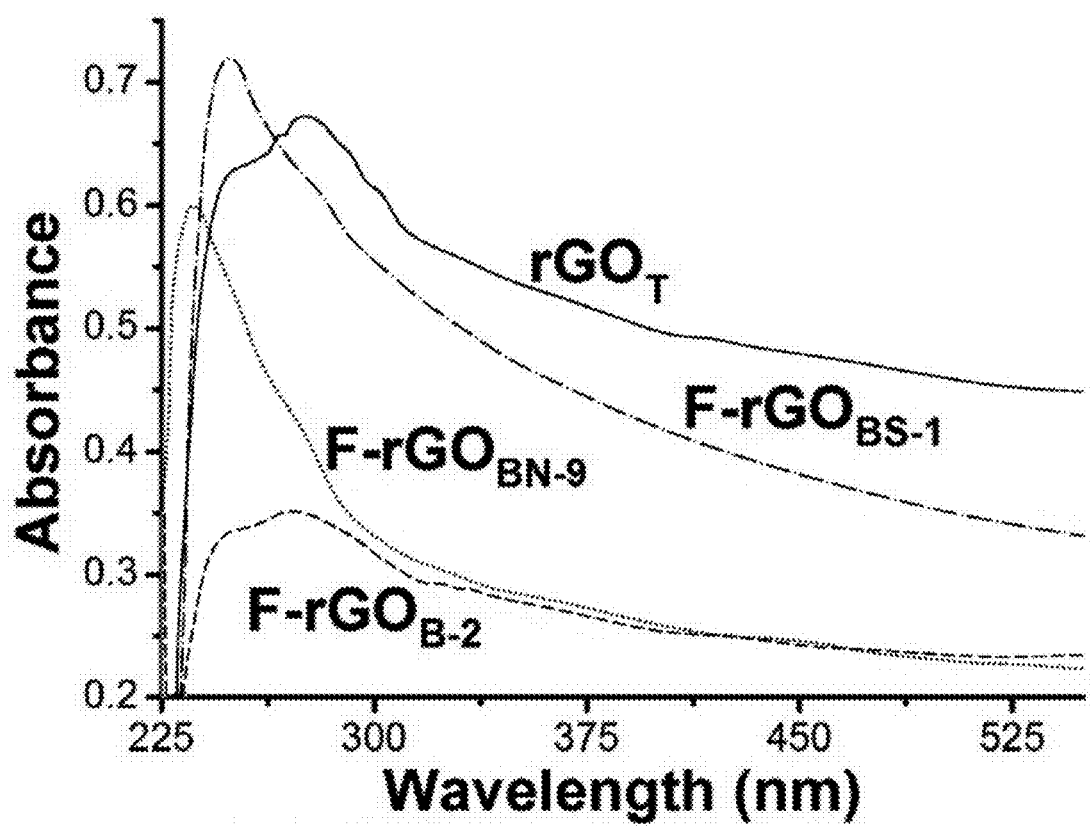
FIG. 3B is a graph that illustrates UV-visible spectra of rGO$_T$, F-rGO$_{B-2}$ (Entry No. 2 of Table 2), F-rGO$_{BS-1}$, and F-rGO$_{BN-9}$ according to examples of methods of synthesizing functionalized graphene.

UV-visible spectroscopy was also used to inspect an effect of the fluorination on π-bond electron arrangement of the GO (FIG. 3B). A thermally heated rGO (rGO$_T$) spectrum exhibited a single broad absorption peak, which is a characteristic of π-π* electronic transition in an aromatic system of rGO$_T$, at 275 nm. After the fluorination, F-rGO$_{B-2}$ (1.4 wt % F), F-rGO$_{BS-4}$ (20 wt % F, FIG. 2A), and F-rGO$_{BN-9}$ (38 wt % F, FIG. 2A) exhibited the absorption peak at 268 nm, 245 nm, and 235 nm, respectively, and exhibited blue shift of 7 nm, 30 nm, and 40 nm, respectively, due to a polarization-induced charge effect (FIG. 3B). It was observed that the surprising blue shift is also sufficiently consistent with the high-percent fluorination obtained by using the method of example embodiments.

Figure 3C:
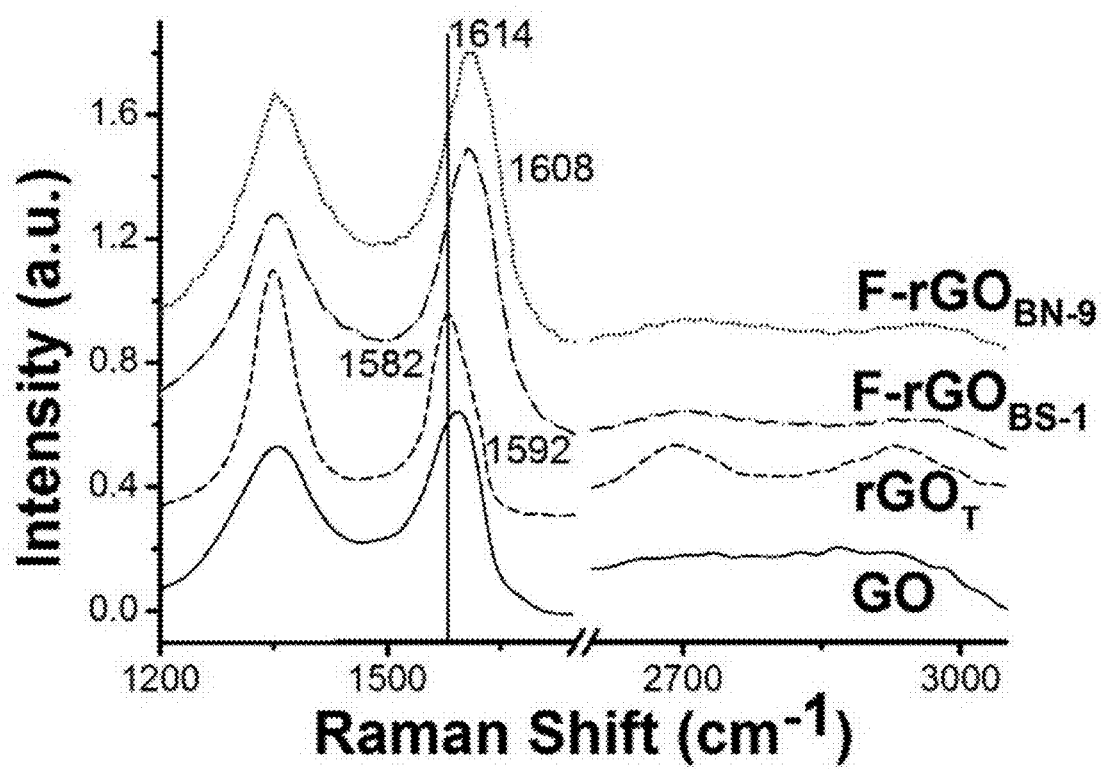
FIG. 3C is a graph that illustrates Raman spectra of GO, rGO$_T$, F-rGO$_{BS-1}$, and F-rGO$_{BN-9}$ according to examples of methods of synthesizing functionalized graphene.

Raman spectroscopy was used to further experiment the effect of the fluorination of the GO by using the present reaction (FIG. 3C). After the fluorination, while a position of G-bond was subject to blue shift, a position of D-bond did not significantly change. When G peaks of the GO and the thermally heated rGO appeared at 1,592 cm$^{-1}$ and 1,582 cm$^{-1}$, respectively, and G peaks of F-rGO$_{BS-1}$ and F-rGO$_{BN-9}$ appeared at 1,608 cm$^{-1}$ and 1,614 cm$^{-1}$, respectively, blue shift of 26 cm$^{-1}$ and 32 cm$^{-1}$ was observed for the GO, and blue shift of 16 cm$^{-1}$ and 22 cm$^{-1}$ was observed for the rGO (FIG. 3C). The blue shift of the G-band position was attributed to phonon curing with F-doping. For 2D and S3 bands, ~2,697 cm$^{-1}$ and ~2,950 cm$^{-1}$ were exhibited, respectively. An intensity ratio $I_D/I_G$ (disordered material) was changed from 0.71 (GO) to 0.90 (0.85 and 0.90 for F-rGO$_{BS-1}$ and F-rGO$_{BN-9}$, respectively) after the reaction. This observation meant that the fluorination, having the blue shift observed in the G-band, occurred with the high % of the present reaction.

Figure 3D:
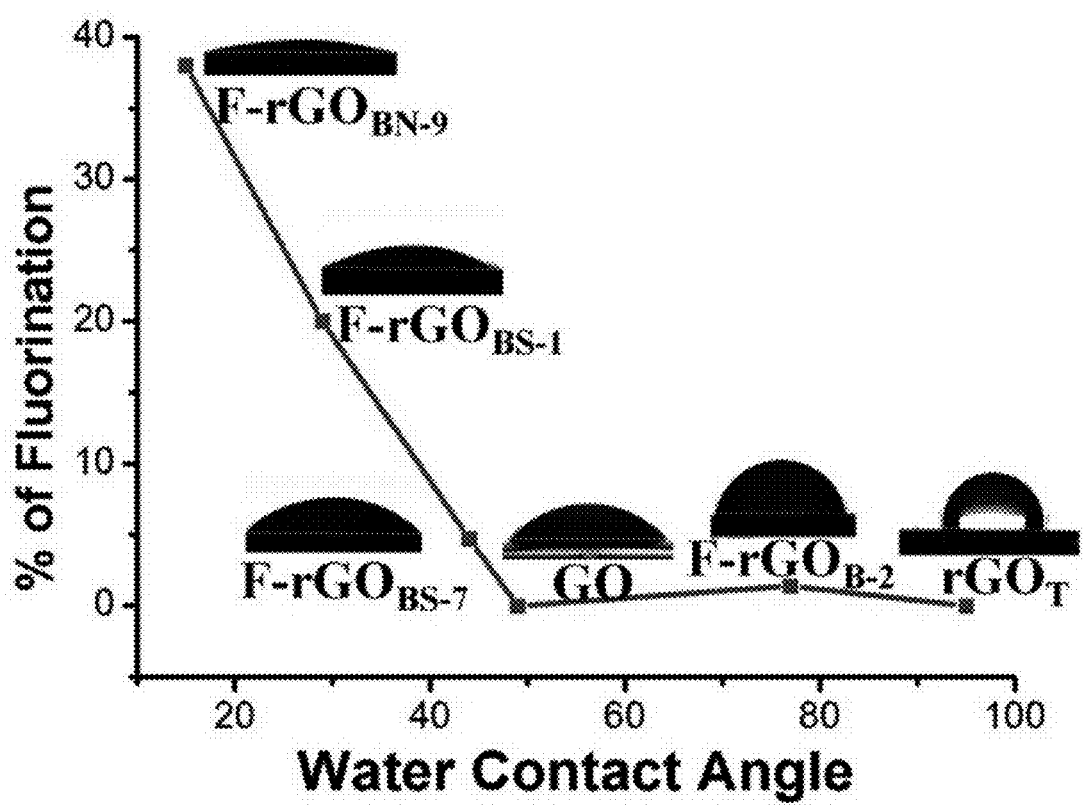
FIG. 3D is a graph that illustrates water contact angles as a function of a fluorination rate according to examples of methods of synthesizing functionalized graphene.

Surface wettability of the fluorinated compound was measured by a water contact angle (WCA). WCAs of rGO$_T$, F-rGO$_{B-2}$, GO, F-rGO$_{BS-7}$, (Entry No. 7 of Table 2, 4.7 wt % F), F-rGO$_{BS-1}$, and F-rGO$_{BN-9}$ were measured as 95°, 77°, 49°, 44°, 29° and 15°, respectively. Accordingly, with the increase of the fluorination, the WCA of the F-rGO surface was reduced from 95° to 15° for the thermally heated rGO (FIG. 3D). A lower contact angle of water is caused by reduction of free surface energy of a solid/liquid surface resulting from hydrogen bond between highly electronegative F-atoms and H-atoms of water. The hydrogen bond also occurred between the doped N-atoms in the F-rGO$_{BN-9}$ sample and water. Meanwhile, like F-atoms and fluorine, H-bond interaction with other doped hydrophilic atoms (e.g., B and N/S) also contributed to the measured reduction of the WCA. When the material of example embodiments has greater wettability, it contributes to high densification of conjugated molecules useful for cell adhesion and growth.

Figure 9A:
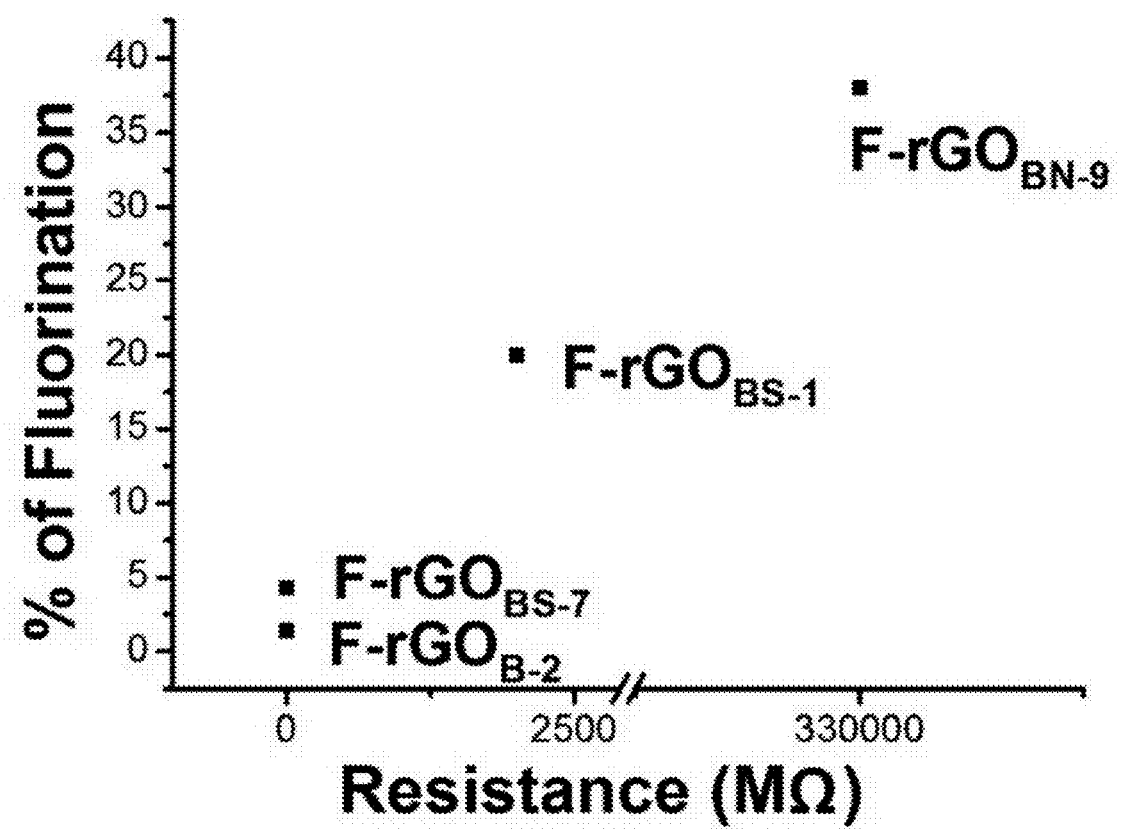
FIG. 9A is a graph showing resistance as a function of fluorination rate according to a number of examples of methods of synthesizing functionalized graphene.
Figure 9B:
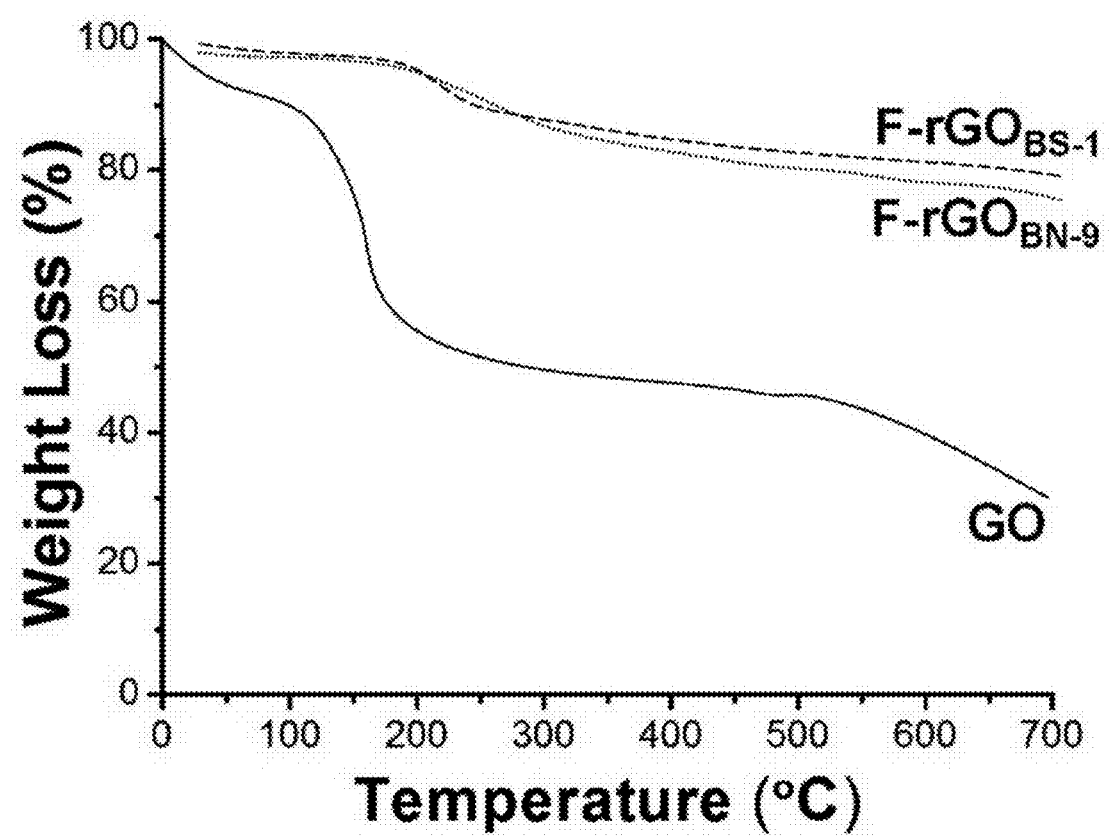
FIG. 9B is a graph that illustrates TGA data for GO, F-rGO$_{BS-1}$, and F-rGO$_{BN-9}$ according to examples of methods of synthesizing functionalized graphene.
Figure 10A:
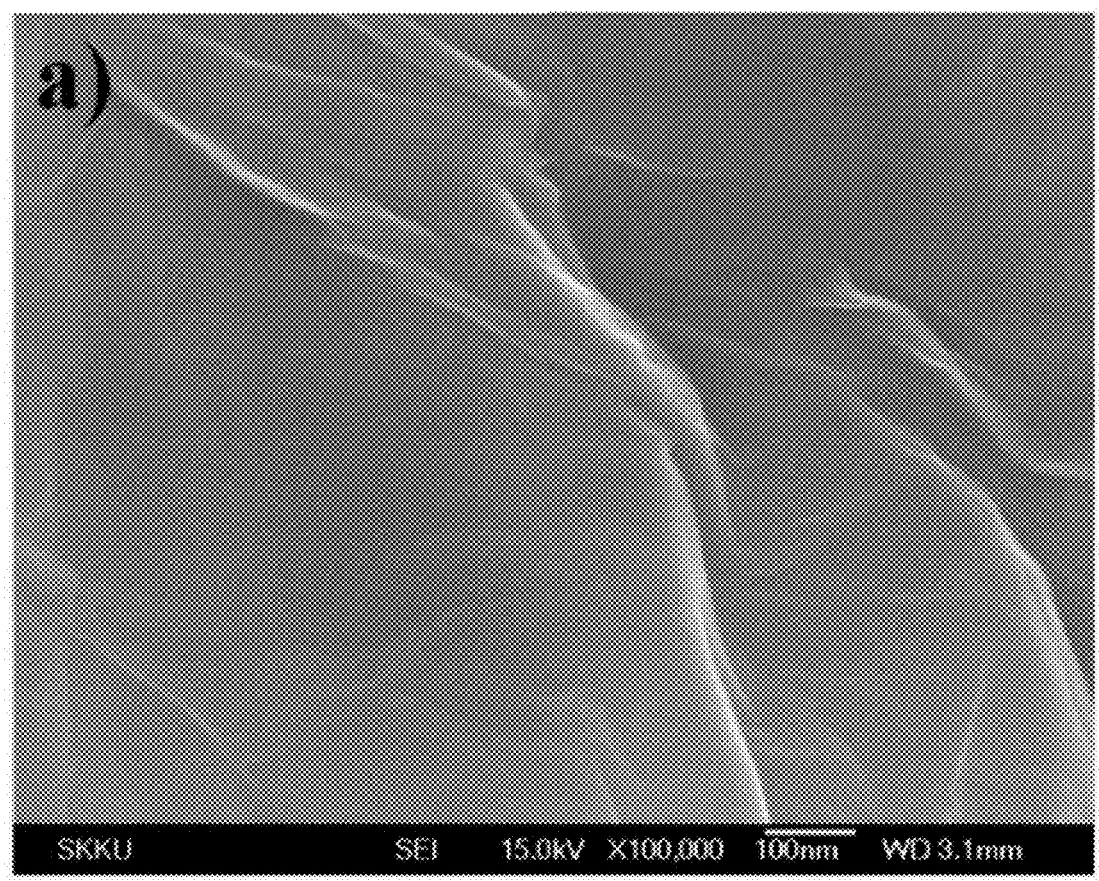
FIG. 10A is SEM image of GO according to an example of a method of synthesizing functionalized graphene.
Figure 10B:
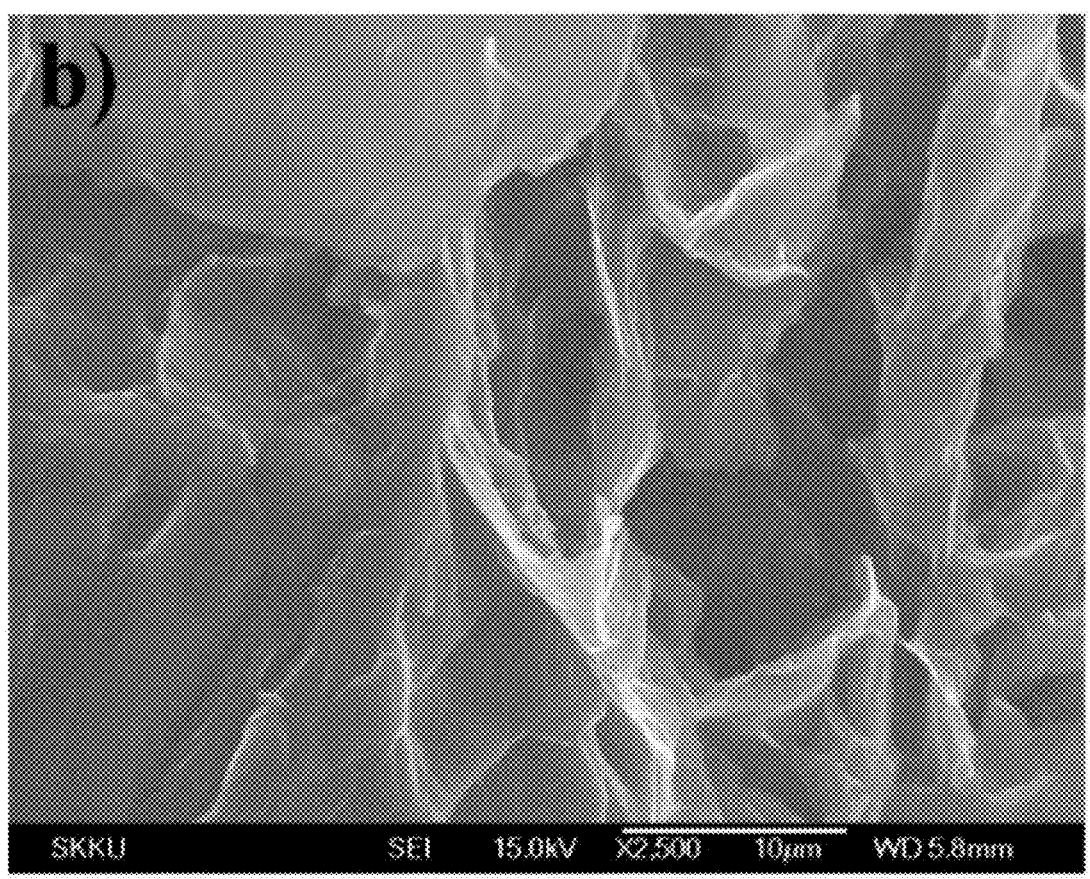
FIG. 10B is SEM image of F-rGO$_{BN-9}$ according to an example of a method of synthesizing functionalized graphene.
Figure 10C:
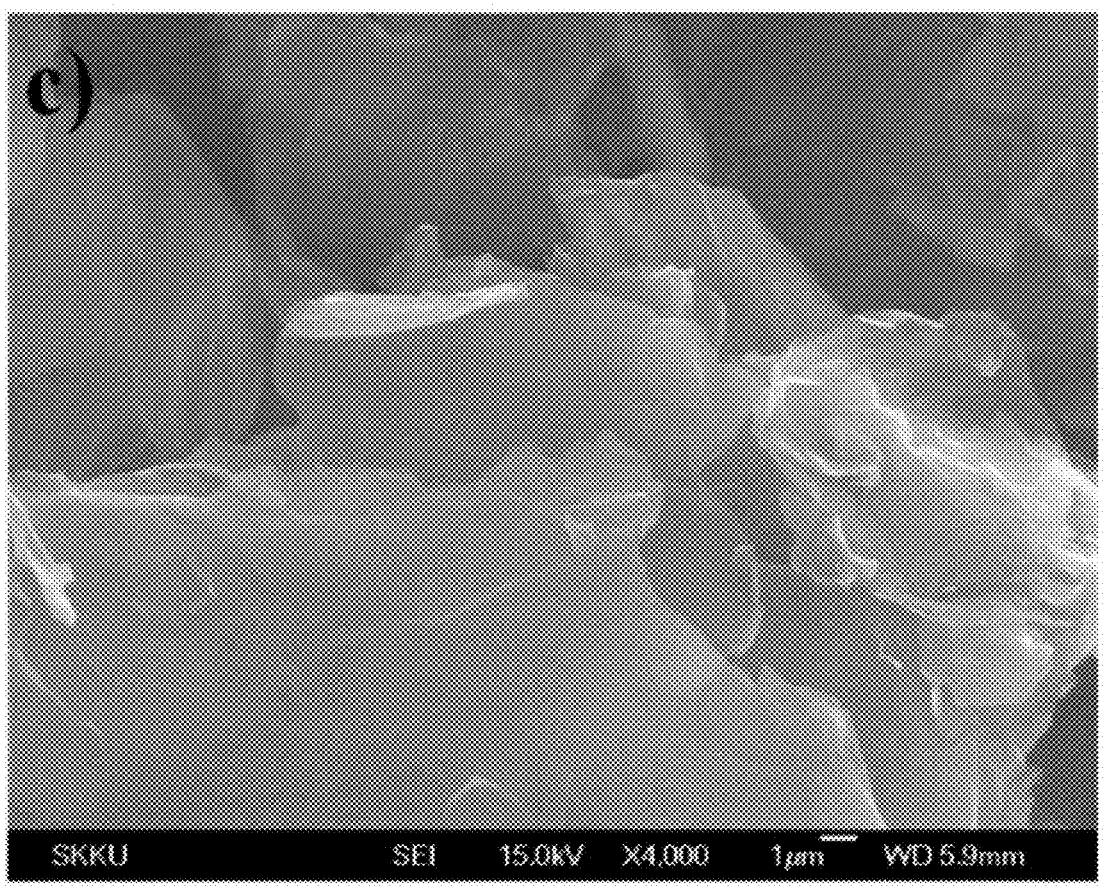
FIG. 10C is SEM image of F-rGO$_{B-2}$ according to an example of a method of synthesizing functionalized graphene.
Figure 10D:
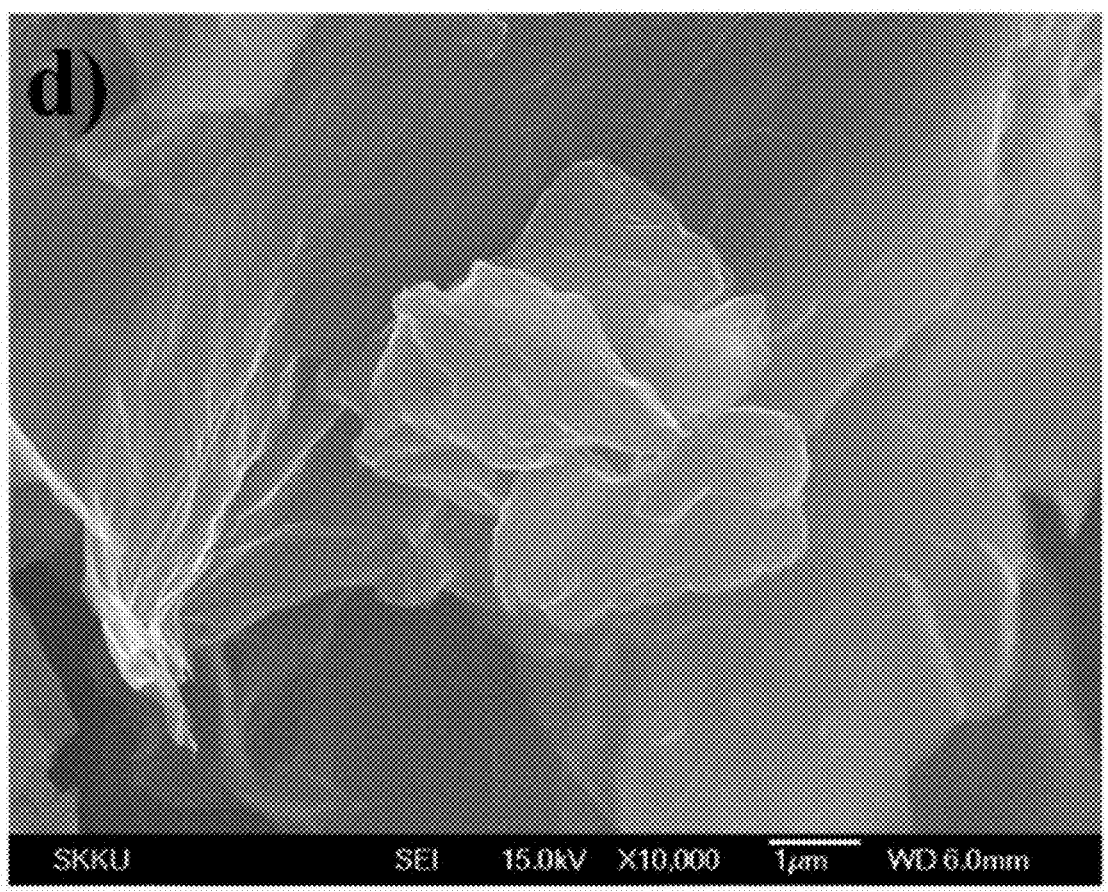
FIG. 10D is SEM image of F-rGO$_{BS-1}$ according to an example of a method of synthesizing functionalized graphene.

FIG. 9A shows variation in resistance depending on a degree of the fluorination. For example, resistance of fluorine-functionalized rGO, like F-rGO$_{B-2}$, F-rGO$_{BS-7}$, F-rGO$_{BS-1}$, and F-rGO$_{BN-9}$, was 0.00002 GΩ, 0.0025 GΩ, 2.0 GΩ, and 330 GΩ, respectively. Accordingly, the resistance rapidly increased with the scope of the fluorination. This high insulation behavior was sufficiently consistent with experiment results for fluorinated graphene synthesized by laser irradiation. Theremogravimetric analysis (TGA) was used to evaluate the properties of the fluorine-functionalized rGO (FIG. 9B). Scanning electron microscope (SEM) images were photographed to identify the shape of the fluorinated rGO prepared by the inventors of the present disclosure. FIGS. 10A to 10D show SEM images of GO, F-rGO$_{BN-9}$, F-rGO$_{B-2}$, and F-rGO$_{BS-1}$.

FIG. 9B shows TGA plots of GO, F-rGO$_{BS-1}$, and F-rGO$_{BN-9}$. In the prepared GO samples, a maximum weight was lost between 100° C. and 200° C., which indicate steam separated in CO, CO$_2$ and the most instable functional group. In the GO, a total weight lost at a temperature of less than 700° C. was approximately 77%. On the other hand, the fluorine-functionalized rGO samples exhibited significantly high thermal stability. For F-rGO$_{BS-1}$ and F-rGO$_{BN-9}$, the total weight lost at the temperature of less than 700° C. was merely 20% and 23%, respectively. This slight weight loss would be attributed mainly to absence of an oxygen functional group.

In conclusion, the inventors of the present disclosure developed an efficient, simple, environment-friendly and solution-based synthesis method for a great deal of fluorination and an in-situ reduction process in a gram scale, and furthermore, presumed simple mechanism. According to one example of the method of producing the functionalized graphene oxide, the functionalized graphene oxide may be produced without the use of NaBH$_4$, concentrated H$_2$SO$_4$ or hydrogen fluoride. Further, the use of high temperature may be avoided. Based on the knowledge of the inventors, this is the first attempt for fluorination of GO using BF$_3$-etherate as a fluorine source. The described method further results in a large amount of F-doped rGO being prepared in a bulk scale for electrical application with suitable memory properties, a high dielectric constant and others. Further, the inventors of the present disclosure have verified that the material prepared by the present disclosure has a high insulation property and high hydrophilicity, and the material is expected to be promising as a viable platform for tissue-engineering application and exhibits high cell adhesion and diffusion. Currently, the inventors of the present disclosure are expecting various application possibilities of the highly fluorinated materials.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

I claim:

1. A method of producing a functionalized reduced graphene oxide, the method comprising:
   (a) a step of dispersing a graphene oxide in an organic solvent; and
   (b) a step of adding BF$_3$-etherate, and at least one co-doping agent selected from the group consisting of alkylthiol, arylthiol, alkylamine and arylamine to the organic solvent in which the graphene oxide is dispersed to produce the functionalized reduced graphene oxide;
   wherein the functionalized reduced graphene oxide comprises reduced graphene oxide which is fluorinated and co-doped with at least one co-dopant selected from the group consisting of B, N and S.

2. The method of claim 1,
   wherein the step (b) is carried out at a temperature between about 30° C. to about 150° C.

3. The method of claim 1,
   wherein the organic solvent comprises tetrahydrofuran, diethyl ether, or ethyl acetate.

4. The method of claim 1,
   wherein the BF$_3$-etherate is used as a fluorinating agent and a reducing agent.

5. The method of claim 4,
   wherein the BF$_3$-etherate is used as a B-doping agent.

6. The method of claim 1,
   wherein the co-doping agent is a nucleophile that acts as a sulfur-doping agent or nitrogen-doping agent.

7. The method of claim 1,
   wherein the step (b) further comprises adding into the organic solvent in which the graphene oxide is dispersed at least one of alkylthiol and arylthiol with at least one of alkylamine and arylamine.

8. The method of claim 1,
wherein the functionalized reduced graphene oxide comprises the reduced graphene oxide which is fluorinated and co-doped with B and N; B and S; or B, N and S.

9. The method of claim 1,
wherein an amount of F due to the fluorination is in a range of from 10 wt % to 40 wt % with respect to the total weight of the functionalized reduced graphene oxide.

10. The method of claim 1,
wherein a C/O ratio in the functionalized reduced graphene oxide ranges from 10 to 20.

11. The method of claim 1,
wherein an amount of the co-dopants ranges from 0.1 wt % to 10 wt % with respect to the total weight of the functionalized reduced graphene oxide.

* * * * *